(12) United States Patent
Owens et al.

(10) Patent No.: US 7,694,593 B2
(45) Date of Patent: Apr. 13, 2010

(54) MULTI-SAMPLE CONDITIONING SYSTEM

(75) Inventors: Aaron M. Owens, Plymouth, MN (US); David Louis Dingmann, St. Paul, MN (US); Steven R. Seeman, Stillwater, MN (US); Troy D. Nickel, Minneapolis, MN (US)

(73) Assignee: Bose Corporation, Framingham, MA (US)

( * ) Notice: Subject to any disclaimer, the term of this patent is extended or adjusted under 35 U.S.C. 154(b) by 80 days.

(21) Appl. No.: 12/119,830

(22) Filed: May 13, 2008

(65) Prior Publication Data

US 2009/0282927 A1    Nov. 19, 2009

(51) Int. Cl.
*G01N 17/00* (2006.01)
(52) U.S. Cl. ........................................ 73/865.6; 73/760
(58) Field of Classification Search ........... 73/760–860, 73/865.6
See application file for complete search history.

(56) References Cited

U.S. PATENT DOCUMENTS

| | | | | |
|---|---|---|---|---|
| 4,648,264 A | * | 3/1987 | Freese et al. | 73/64.41 |
| 5,360,267 A | * | 11/1994 | Ibar | 374/45 |
| 5,659,140 A | * | 8/1997 | Jakob et al. | 73/788 |
| 5,710,426 A | * | 1/1998 | Reed et al. | 250/237 G |
| 5,959,215 A | * | 9/1999 | Ono et al. | 73/798 |
| 6,332,364 B1 | * | 12/2001 | Buschmann et al. | 73/788 |
| 6,405,599 B1 | | 6/2002 | Patt | |
| 7,059,198 B2 | * | 6/2006 | Dharia | 73/821 |
| 2003/0199083 A1 | | 10/2003 | Vilendrer et al. | |
| 2004/0219659 A1 | | 11/2004 | Altman et al. | |
| 2005/0153436 A1 | | 7/2005 | Vilendrer | |

FOREIGN PATENT DOCUMENTS

| | | |
|---|---|---|
| DE | 9214659 | 11/1993 |
| WO | 2007013972 | 2/2007 |
| WO | 2007082050 | 7/2007 |

OTHER PUBLICATIONS

International Search Report and Written Opinion dated Apr. 6, 2009 for PCT/US2008/084538.

* cited by examiner

*Primary Examiner*—Max Noori

(57) ABSTRACT

A multi-sample conditioning system may include a sample chamber for each sample or a sample chamber holding one or more samples. Multiple samples enable replication for statistical analysis and individual sample chambers enable individual nutrient flow profiles for each sample. A mechanical imbalance may be created when a sample chamber is removed or when samples of different stiffness are conditioned together. The mechanical imbalance may result in an undesired alteration of the desired conditioning profile and increase the variation in the conditioning profile applied to each sample. An asymmetric-loading support assembly provides a low friction support to reduce the undesired alteration of the desired conditioning profile applied to the samples and reduce unwanted reaction loads on the conditioning drive mechanisms. The asymmetric-loading support assembly preferably includes a flexure as the low-friction, high-stiffness support. Other examples that can provide low-friction, high-stiffness support include air bearings, magnetic bearings, and hydraulic bearings.

4 Claims, 7 Drawing Sheets

MULTI-SAMPLE CONDITIONING SYSTEM

BACKGROUND

This disclosure relates to systems and methods for a multi-sample conditioning system. The sample may be a biologic material, a synthetic material, or a combination of a biologic material and a synthetic material. Examples of a biologic material include native tissue, processed tissue, cell-seeded biomaterial scaffolds, and tissue-engineered constructs. Examples of a synthetic material include medical devices and acellular biomaterials and scaffolds.

SUMMARY

A multi-sample conditioning system may include a sample chamber for each sample or a sample chamber holding one or more samples. Multiple samples enable replication for statistical analysis and individual sample chambers enable individual nutrient flow profiles for each sample. A mechanical imbalance may be created when a sample chamber is removed or when samples of different stiffness are conditioned together. The mechanical imbalance may result in an undesired alteration of the desired conditioning profile and increase the variation in the conditioning profile applied to each sample. An asymmetric-loading support assembly provides a low friction support to reduce the undesired alteration of the desired conditioning profile applied to the samples and reduce unwanted reaction loads on the conditioning drive mechanisms. The asymmetric-loading support assembly preferably includes a flexure as the low-friction, high-stiffness support. Other examples that can provide low-friction, high-stiffness support include air bearings, magnetic bearings, and hydraulic bearings.

One embodiment of the present invention is directed to a system comprising a conditioning frame configured to hold at least one sample chamber and stimulate a sample held in the at least one sample chamber according to a user-defined conditioning profile, the conditioning profile generated by an actuator mechanically coupled to the sample in the at least one sample chamber, the conditioning frame including an asymmetric-loading support assembly configured to reduce a deviation in a conditioning profile applied to the sample from the user-defined conditioning profile resulting from an unbalanced load configuration of the at least one sample chamber. In an aspect, the conditioning profile is a strain profile. In a further aspect, the conditioning profile is characterized by a strain profile, the strain profile repeatedly applied to the sample. In another aspect, the actuator is a moving magnet linear motor. In another aspect, the conditioning frame further includes a push-bar assembly mechanically coupled to the actuator and to each sample in each of the at least one sample chamber mounted on the conditioning frame. In another aspect, the asymmetric-loading support assembly includes a support rod having a first end rigidly coupled to the actuator and a second end coupled to the conditioning frame with a low-friction, high rigidity support. In a further aspect, the low-friction, high rigidity support is a flexure. In a further aspect, the low-friction, high rigidity support is a magnetic bearing. In a further aspect, the low-friction, high rigidity support is an axially soft and radially rigid coil/torsion spring. In another aspect, the at least one sample chamber holds a plurality of samples, each of the plurality of samples mechanically coupled to the actuator and stimulated according to the user-defined conditioning profile.

DETAILED DESCRIPTION

Figure 1:
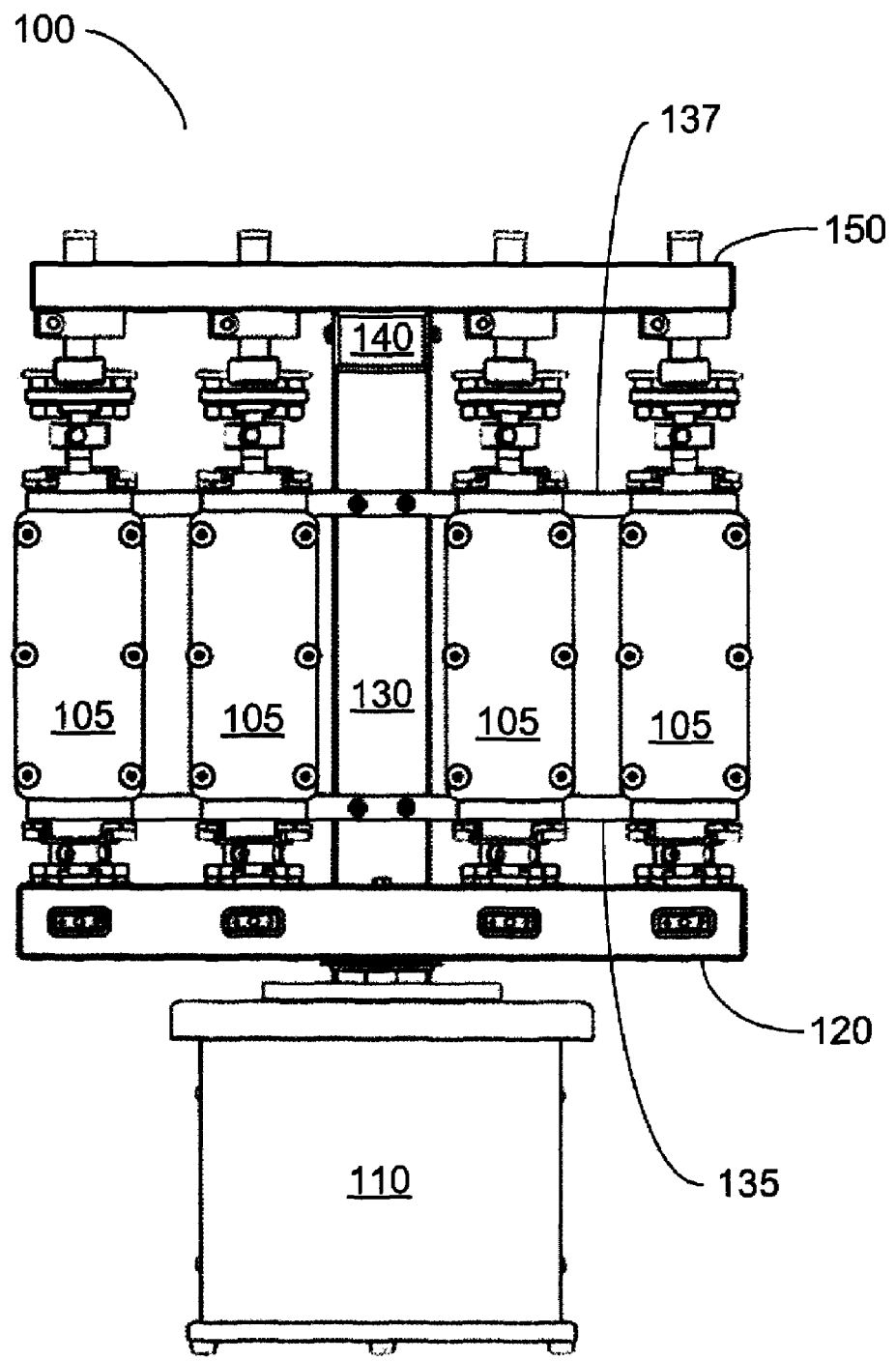
FIG. 1 is a front view of a portion of a multi-sample conditioning system.

FIG. 1 illustrates a front view of a conditioning frame 100 of a multi-sample conditioning system. The conditioning frame 100 includes a power-head assembly 110, push-bar assembly 120, a load-frame beam 130, a reaction bracket 140, and a reaction crossbar 150. The power-head assembly 110 is rigidly attached to the load-frame beam 130. The load-frame beam 130 is attached to the reaction bracket 140. The reaction bracket 140 supports the crossbar 150. The load-frame beam 130 supports a lower chamber mounting bar 135 and an upper chamber mounting bar 137. In the example shown in FIG. 1, the upper and lower mounting bars support four sample chambers 105 but is not limited to four sample chambers.

The power-head assembly 110 includes a rigid housing attached to the load-frame beam 130 and an actuator (not shown) mounted to the rigid housing. The actuator drives the push-bar assembly 120. Although FIG. 1 shows a linear arrangement of sample chambers, other configurations of sample chambers may also be used. For example, the sample chambers may be arranged in a radial or circumferential pattern. In other configurations, a sample chamber may support multiple samples. In other configurations, any number of sample chambers may be used to hold the multiple samples.

The actuator is preferably a linear motor and more preferably a moving magnet linear motor although other actuators may be used in other embodiments. An example of a moving magnet linear motor is disclosed in U.S. Pat. No. 6,405,599 issued on Jun. 18, 2002 herein incorporated by reference in its entirety. Examples of other types of actuators that may be used include but are not limited to a voice coil, a linear servomotor, a rotary motor with a drive mechanism, a hydraulic actuator, a pneumatic actuator, and a piezo-electric actuator. The push-bar assembly 120 couples a axial displacement of the push-bar assembly 120 to a sample grip inside the sample chamber 105.

Figure 2:
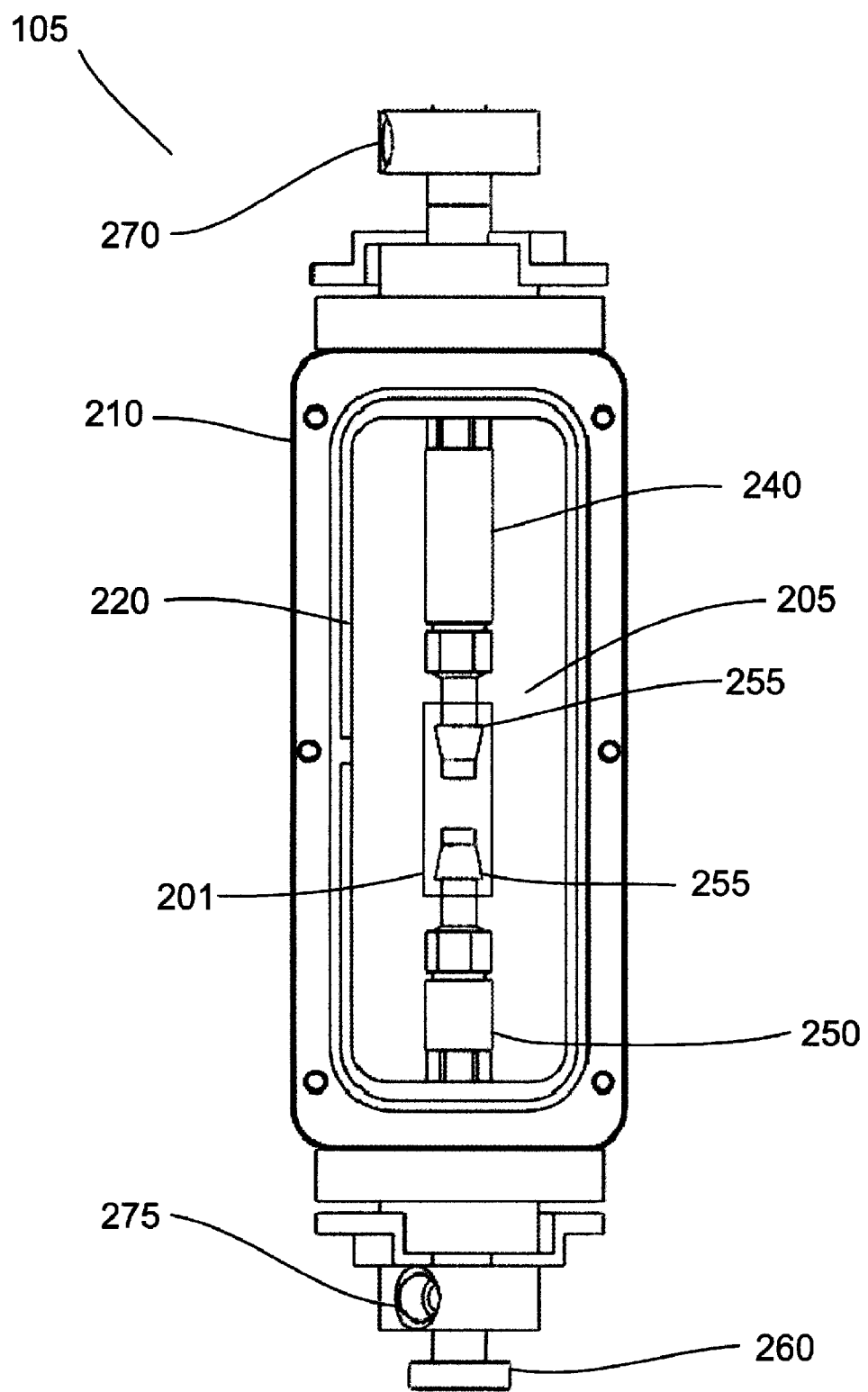
FIG. 2 is a front view of a sample chamber.

FIG. 2 illustrates a front view of a sample chamber 105. The sample chamber 105 includes a chamber housing 210 that encloses a chamber volume 205. The chamber housing 210 may include a chamber window 220 allowing visual monitoring and measurement of the sample 201 during a process run. The sample chamber may be configured to accommodate a variety of sample grips according to the type of sample. For example, pincher-type grips may be used to hold a strip such as a ligament or tendon sample or porous or non-porous platens may be used to hold disk-shaped samples or three- or four-point bend fixtures may be used to condition samples in the chamber. In the configuration shown in FIG. 2, an upper sample grip 240 and a lower sample grip 250 are configured to hold a tubular sample 201. The tubular sample grips each have an end fitting 255 such as, for example, a nozzle or barb fitting that holds an end of the tubular sample. The sample grips 240, 250 may be hollow to allow nutrient flow through the lumen during the conditioning protocol. Chamber ports 270, 275 provide fluid communication between the lumen flow and an external nutrient fluid circuit. A second fluid circuit may be provided to enable independent fluid flow through the chamber volume 205. The details of the nutrient fluid management system and control along with the instrumentation and system controls that may be used is described in co-pending U.S. application Ser. No. 11/780,729, filed Jul. 20, 2007, herein incorporated by reference in its entirety.

In FIG. 2, the lower sample grip 250 is mechanically coupled to a lower mounting flange 260. The lower mounting flange 260 fits in a mounting assembly on the push-bar assembly such that the lower sample grip 250 is mechanically coupled to the push-bar assembly. The lower sample grip 250 is free to move relative to the chamber housing 210 and mechanically transmits a user-defined conditioning profile generated by the actuator to the held sample. The upper sample grip 255 may be configured to allow movement relative to the chamber housing 210 and may be attached to a measurement transducer such as a force transducer. In the configuration shown in FIG. 2, as the push-bar assembly is displaced axially by the actuator, the axial displacement of the push-bar assembly creates an axial strain on the sample held by the lower sample grip. The actuator may be operated by a controller to apply a user-defined conditioning profile to the sample.

The user-defined conditioning profile specifies the desired mechanical stimulation of the sample. The conditioning profile may specify a desired stress or strain state applied to the sample and may vary in time. If a cyclic conditioning protocol is desired, the conditioning profile may describe a desired stress or strain state over a user-specified cycle and the profile repeated for a user-specified number of cycles. Using the configuration shown in FIG. 1 as an example, a user may desire to apply a cyclic strain to the samples. The desired strain may be converted to a displacement of the cross-bar assembly and the actuator operated to provide the displacement of the cross-bar assembly to produce the desired strain conditioning on each sample. In another example, a bellows may be coupled to the lower sample grip and inline with the flow circuit providing fluid flow through a tubular sample. The cross-bar assembly may be coupled to the bellows such that cyclic displacement of the cross-bar assembly operates the bellows to create a pulsatile flow through a tubular sample.

In the embodiment shown in FIG. 1, up to four sample chambers may be used during the conditioning procedure. In some conditioning protocols, the samples may be subjected to the same nutrient flow profile and the same conditioning profile to provide replicated data for statistical analysis. During a conditioning protocol, a sample chamber may be removed from the conditioning frame for detailed examination of the sample while the remaining samples continue the conditioning protocol.

Figure 3:
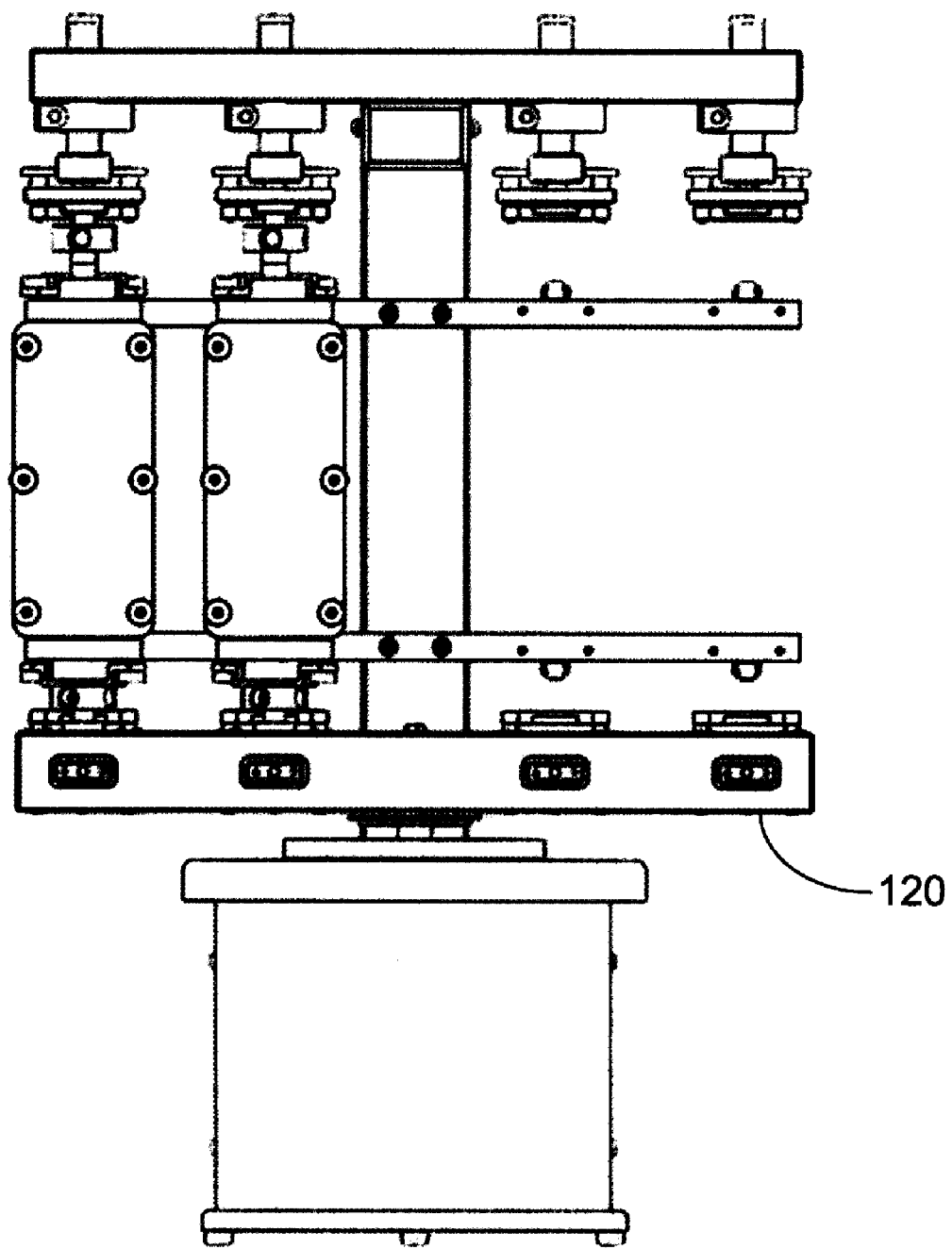
FIG. 3 is a front view of the conditioning system of FIG. 1 with the two rightmost sample chambers removed.

FIG. 3 is a front view of the embodiment shown in FIG. 1 illustrating an unbalanced load configuration where the two rightmost sample chambers have been removed. When a sample chamber is removed from the conditioning frame, the push-bar assembly 120 experiences an asymmetric loading condition caused by the removed chambers. The asymmetric loading condition on the push-bar assembly is manifested as a bending moment on an actuator shaft coupling the push-bar assembly to the actuator that transmits the bending moment to the actuator. The bending moment may result in increased angular distortion on the actuator, actuator shaft and push-bar assembly that may alter the conditioning profile applied to the samples. The distortion may also reduce the lifetime of the actuator shaft or bearing assembly coupling the actuator to the push-bar assembly. Run protocols may have durations spanning several months and a fatigue-type failure may result in the loss of the samples and the time invested in the failed process run. Furthermore, the altered load profile may affect the samples and introduce an unknown bias to the statistical analysis of the samples.

The asymmetric loading condition may also arise when samples of different stiffness are conditioned together. In some conditioning protocols, samples of different stiffness may be subjected to the same nutrient flow profile and the same conditioning profile. In many situations, the stiffness of a biological sample varies by 20% between samples. In other situations, different types of samples having different stiffness may result in configurations where the sample-to-sample stiffness varies by 100% or more. When conditioned together, a first sample characterized by a high stiffness relative to a second sample will resist the movement of the push-bar assembly more than the relatively low stiffness second sample causing the push-bar assembly to rotate. The rotation of the push-bar assembly in response to the asymmetric loading condition increases the variation in the conditioning profile between each sample. For example, a user may desire a 1 mm peak-to-peak axial displacement sinusoid applied to each sample but because of an asymmetric loading condition, one sample may experience a 0.90 mm axial displacement while a companion sample experiences a 1.2 mm axial displacement.

Bushings or linear bearings may be used to restrict movement of the actuator shaft to allow only axial movement and prevent lateral displacement of the shaft but the bending moment generated by the asymmetric loading on the push-bar assembly is applied to the bushings or linear bearings and can result in decreased fatigue lifetime of the bushing or linear bearings. Furthermore, the frictional forces on the bushings or linear bearings can alter the conditioning profile applied to the sample from the user-desired conditioning profile.

Figure 4:
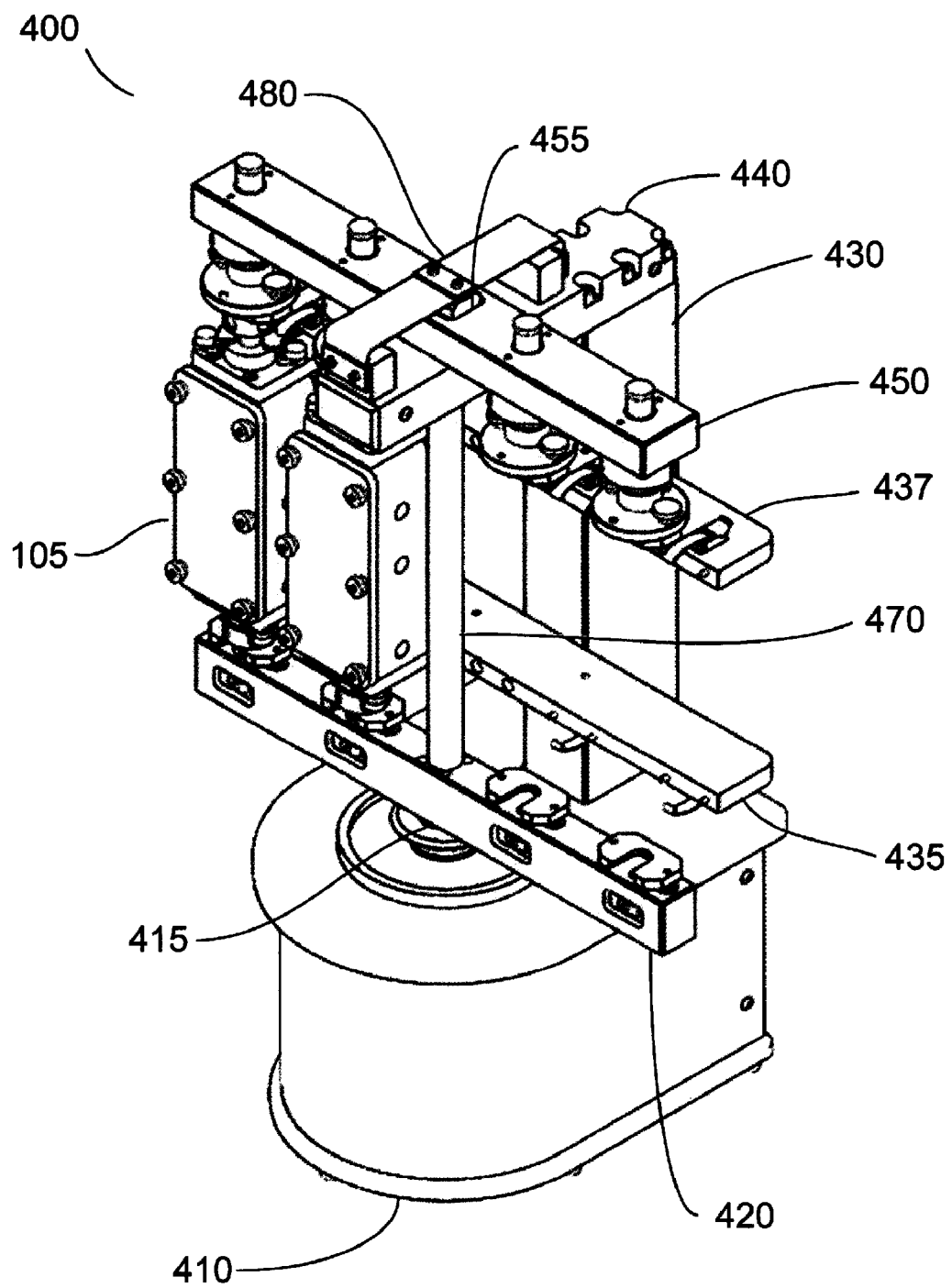
FIG. 4 is an isometric view of another embodiment of a multi-sample conditioning system.

FIG. 4 illustrates a perspective view of another embodiment of a conditioning frame. In FIG. 4, the conditioning frame 400 is shown with the two rightmost sample chambers and the flexure housing removed to more clearly show an off-axis support assembly. In FIG. 4, power-head assembly 410 houses an actuator and a displacement sensor (not shown). The actuator is mechanically coupled to a push-bar assembly 420 through an opening 415 in the power-head assembly 410. In the configuration shown in FIG. 4, up to four sample chambers 105 may be mounted to an upper load-frame mounting bar 437 and a lower load-frame mounting bar 435. The upper and lower load-frame mounting bars 437, 435 are rigidly supported by a load-frame upright beam 430. The load-frame upright beam 430 is attached to the power-head assembly 410 and maintains the sample chambers 105 in a stationary position relative to the power-head assembly 410. The load-frame upright beam 430 supports load-frame reaction bracket 440 and reaction crossbar 450. The reaction crossbar 450 is mechanically coupled to an upper sample grip (not shown) in the sample chamber 105 and maintains the upper sample grip in a stationary position relative to the power-head assembly 410.

The actuator may be operated to follow a cyclic loading profile that is transmitted through the push-bar assembly 420 to each of the lower sample grips inside each mounted sample chamber 105.

An asymmetric-load support assembly includes a support rod 470 that is rigidly attached to the push-bar assembly 420 and is preferably co-linear with an axis of the actuator. The other end of the support rod 470 is attached to a low-friction, high-rigidity support such as a flexure 480 through an opening 455 through the load-frame reaction bracket 440 and reaction crossbar 450. The flexure 480 is mounted to the reaction bracket 440. As the actuator pushes the push-bar assembly 420, the support rod 470 is pushed upward causing the flexure 480 to bend upward to accommodate the upward movement of the support rod 470 while keeping the support rod 470 centered in the opening 455. If the cross-bar assembly 415 rotates in response to an asymmetric loading condition, the end of the support rod 470 attached to the low-friction, high-rigidity support would exhibit a lateral displacement if it were not attached to the low-friction, high rigidity support. The low-friction, high rigidity support restricts the lateral displacement of the support rod end and generates a reaction force that opposes the rotation of the cross-bar assembly 415.

In the example shown in FIG. 4, the flexure is a U-shaped structure preferably comprising a material that remains in its elastic region over the expected peak-to-peak axial displacement of the support rod. For example, metal alloys such as steel alloys, nickel alloys, or aluminum alloys, may be used for the flexure. Engineering plastics or polymer composites may also be used depending on the fatigue cycle profile and lifetime desired for the flexure. The flexure is sized to provide little resistance to the axial movement of the support rod while providing stiff resistance to lateral movement of the support rod. The U-shaped flexure guides a moving element along a linear axis but other flexure shapes may be used.

Figure 5:
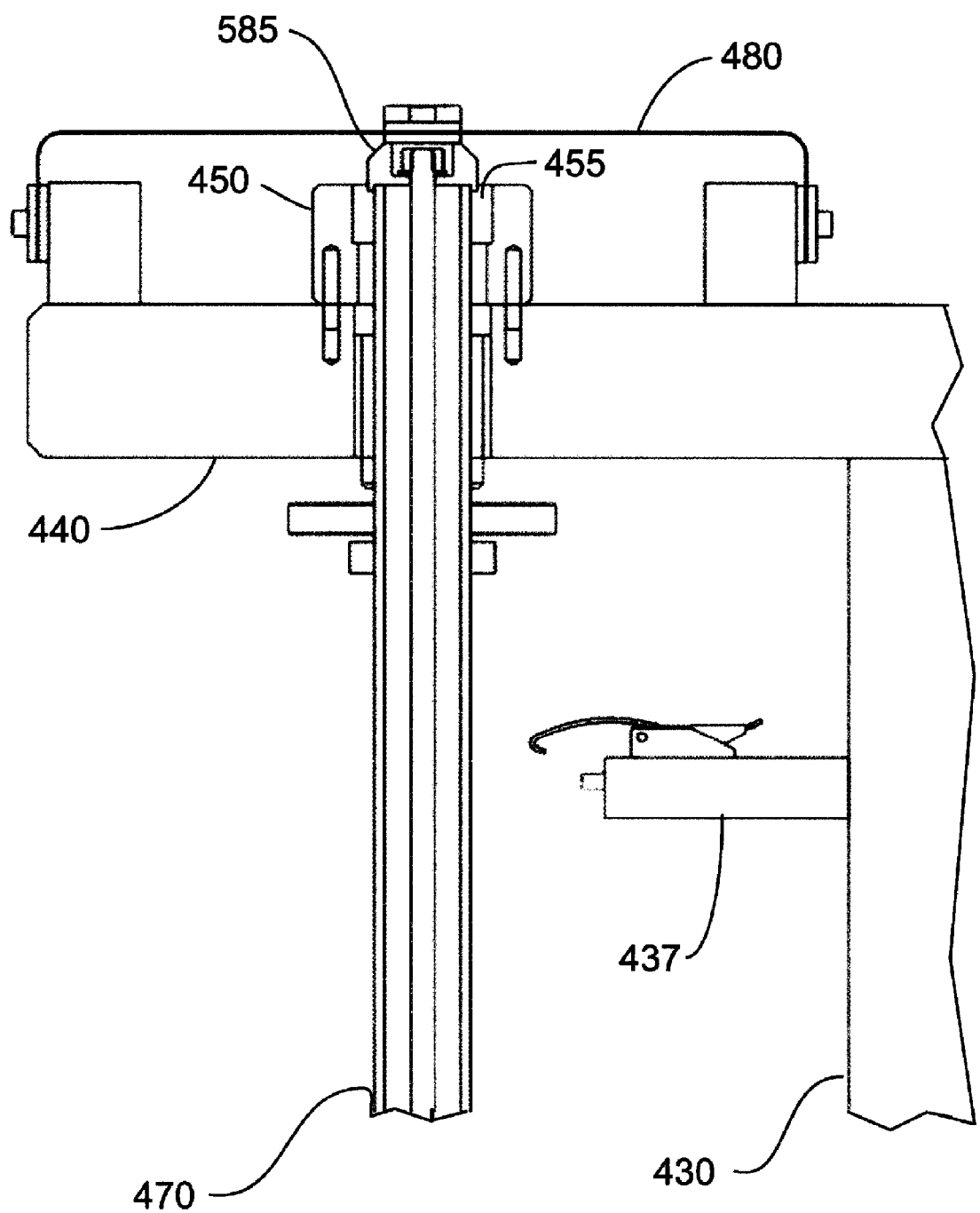
FIG. 5 is a sectional side view of a portion of the reaction crossbar and flexure shown in FIG. 4

FIG. 5 is a sectional side view of a portion of the reaction crossbar and flexure shown in FIG. 4 where the same reference number refers to the same structure shown in FIG. 4. In FIG. 5, the support rod 470 is mechanically coupled to the flexure 480 with a mounting block 585. The opening 455 is sized to allow free movement of the mounting block 585 when the flexure is flexed downward.

Figure 6:
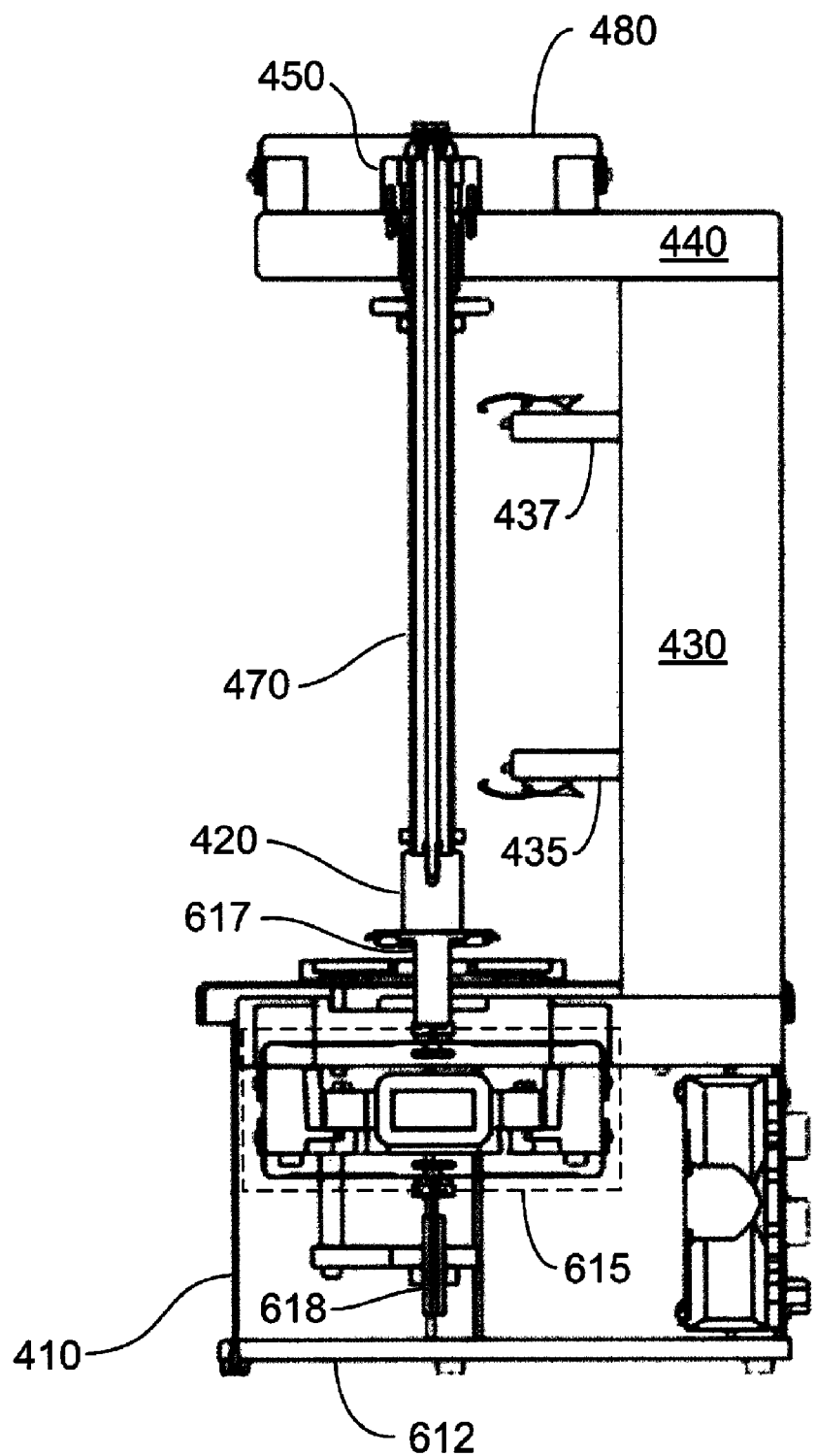
FIG. 6 is a sectional side view of the conditioning frame shown in FIG. 4

FIG. 6 is a sectional side view of the conditioning frame shown in FIG. 4 where the same reference number refers to the same structure shown in FIG. 4. In FIG. 6, an actuator 615 is mounted to a housing 612 of the power-head assembly 410. In the embodiment shown in FIG. 6, the actuator 615 is a moving magnet linear motor but any actuator capable of generating a reciprocating linear motion may be used. An actuator shaft 617 mechanically couples the actuator 615 to the push-bar assembly 420. A linear displacement sensor 618 is coupled to the actuator 615 to measure the displacement of the cross-bar assembly 420.

Having thus described at least illustrative embodiments of the invention, various modifications and improvements will readily occur to those skilled in the art and are intended to be within the scope of the invention. For example, although a flexure has been described as a method of reducing the effect of asymmetric loading, other embodiments may substitute the flexure with other types of low-friction, high-rigidity supports such as air bearings, magnetic bearings or axially soft and radially rigid coil/torsion springs. Furthermore, although an axial stress configuration has been described, other embodiments may include stimulating the sample by torsion, bending, radial or other strain profiles. It should be appreciated that the teachings herein are not limited to sample chambers holding a single specimen and other embodiments may include mechanically stimulating multiple specimens within a single sample chamber such as those described in co-pending U.S. application Ser. No. 11/780,729, filed Jul. 20, 2007.

Figure 7:
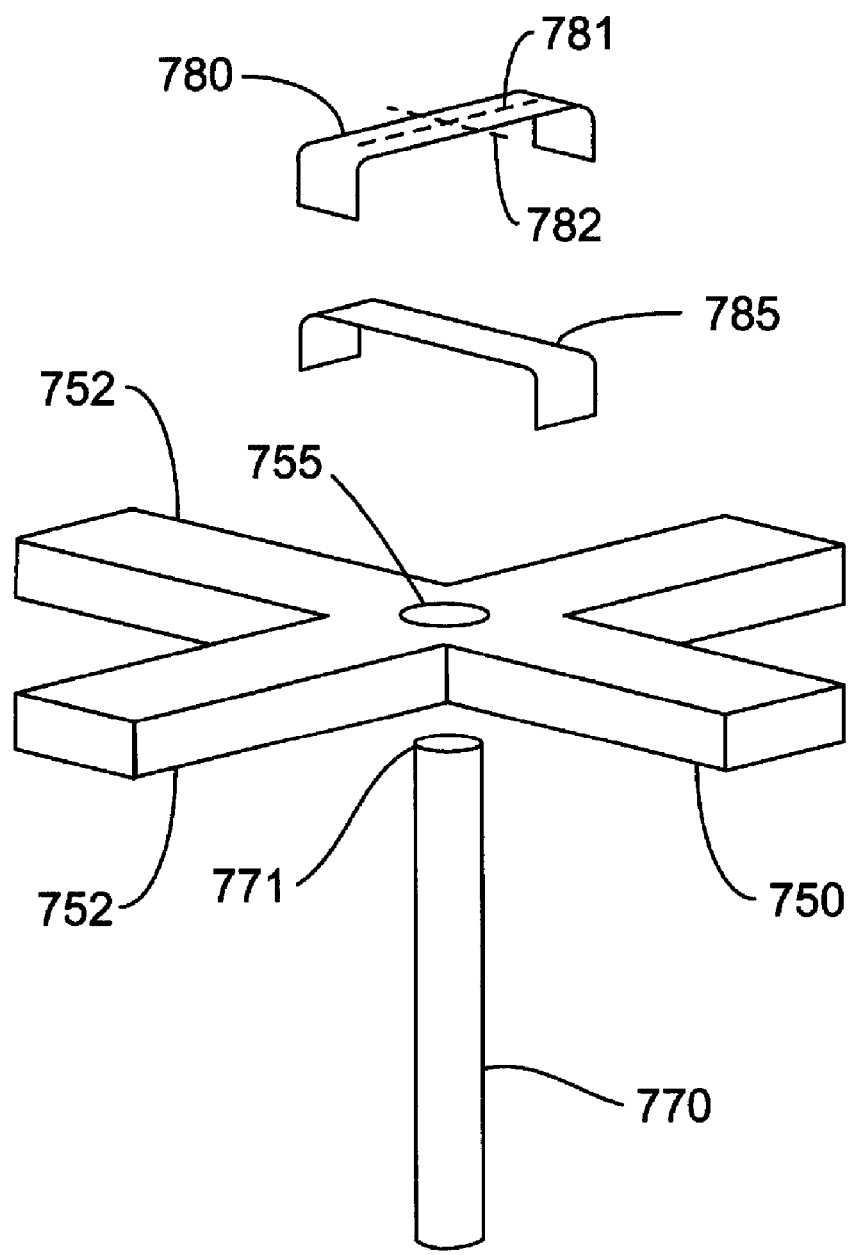
FIG. 7 is an exploded view of a portion of another embodiment of a multi-sample conditioning system.

Furthermore, other flexure designs may be used accommodate other configurations of sample chambers. For example, FIG. 7 illustrates an exploded view of a portion of an asymmetric-loading support assembly that uses a crossed flexure that may be used in a radial configuration of sample chambers. In FIG. 7, the asymmetric-loading support assembly includes a support rod 770, a first U-shaped flexure 780 and a second U-shaped flexure 785 that are crossed at the center of each flexure and are mechanically connected an end 771 of support rod 770 at the center of the crossed flexure. The support rod 770 is free to move axially relative to a reaction cross-bar 750 through an opening 755 in the reaction cross-bar 750. Each end 788 of the crossed flexure is rigidly attached to the reaction cross-bar 750 that forms a portion of the conditioning frame and provides a stationary reference with respect to the moving support rod 770 driven by the actuator (not shown). The reaction cross-bar 750 shown in FIG. 7 shows four arms 752 that support one or more sample chambers (not shown) in a radial configuration. Each arm 752 may support one or more sample chambers. Although the arms 752 are arranged in a balanced pattern with a first arm balanced by a second arm on the opposite side of the first arm, other patterns such as a reaction cross-bar having three or five arms may also be used. Each U-shaped flexure 780, 785 may be characterized by long axis 781 and a short axis 782. The U-shaped flexure is stiff in directions along the long axis 781 and along the short axis 782 relative to the stiffness in the axial direction. The stiffness along the short axis 782, however, is larger than the stiffness along the long axis 781. In the configuration shown in FIG. 7, the short axis of the first U-shaped flexure 780 is oriented to be parallel to two of the arms of the reaction cross-bar 750 and the short axis of the second U-shaped flexure 785 is oriented to be parallel to the other two arms of the reaction cross-bar 750. Without being limiting, the crossed flexure shown in FIG. 7 is believed to provide large resistance to any bending moments arising from asymmetric loading conditions such as, for example, unbalanced sample chambers or samples exhibiting different stiffness characteristics. Although the stiffness along the short axis is larger than the stiffness along the long axis, the stiffness along the long axis may be sufficient to constrain the lateral movement of the support rod along the long axis. In such a situation, a single U-shaped flexure may be sufficient as the low-friction, high rigidity support.

Accordingly, the foregoing description is by way of example only and is not intended as limiting. The invention is limited only as defined in the following claims and the equivalents thereto.

What is claimed:

1. A system for applying mechanical stimulation to a plurality of samples, the system comprising:

a plurality of sample chambers, each having first and second sample grips therein;

a support structure for removably holding at least two of the sample chambers in fixed positions relative to an actuator;

a push-bar assembly having mechanical couplings, along a first axis, for transmitting force from the actuator to the first sample grips of as many sample chambers as are coupled to the support structure;

a reaction crossbar coupled to the support structure and having mechanical couplings for supporting the second sample grips of as many sample chambers as are coupled to the support structure;

a flexure mounted to the support structure, the flexure allowing motion in a first direction with low friction and having high-rigidity resisting motion in at least one second direction; and a support rod having a linear axis, rigidly coupled at a first end to the push-bar assembly and coupled at a second end to the flexure;

the flexure, through the support rod, allowing motion of the push-bar assembly parallel to the linear axis of the support rod and resisting rotation of the push-bar assembly in a plane defined by the push-bar's first axis and the support rod's linear axis.

2. The system of claim 1 wherein the flexure controls motion of the push-bar assembly by allowing linear motion of the support rod along the support rod's linear axis and resisting lateral motion of the support rod.

3. The system of claim 1 wherein the flexure comprises a generally U-shaped band rigidly fixed to the support structure at first and second ends of the U-shape and fixed to the support rod at the center of the U-shape, wherein the flexure is formed of a material remaining in an elastic region over an expected peak-to-peak axial displacement of the support rod while providing stiff resistance to lateral movement of the support rod.

4. The system of claim 1 further comprising:

a second support structure for removably holding at least two additional sample chambers in fixed positions relative to the actuator;

a second push-bar assembly having mechanical couplings, along a second axis, for transmitting force from the actuator to the first sample grips of as many sample chambers as are coupled to the second support structure;

a second flexure mounted to the first or second support structure, the second flexure, through the support rod, allowing motion of the second push-bar assembly parallel to the linear axis of the support rod and resisting rotation of the second push-bar assembly in a second plane defined by the second axis and the support rod's linear axis.

* * * * *